United States Patent [19]

Raible

[11] Patent Number: 4,597,756
[45] Date of Patent: Jul. 1, 1986

[54] ANGULAR IMPLANT DEVICE

[75] Inventor: Donald A. Raible, Irvine, Calif.

[73] Assignee: American Hospital Supply Corp, Evanston, Ill.

[21] Appl. No.: 725,313

[22] Filed: Apr. 19, 1985

Related U.S. Application Data

[60] Division of Ser. No. 624,801, Jun. 26, 1984, Pat. No. 4,534,760, which is a continuation of Ser. No. 292,844, Aug. 14, 1981, abandoned.

[51] Int. Cl.⁴ .................... A61M 5/32; A61M 25/00; A61M 5/00
[52] U.S. Cl. ........................................ 604/175; 604/8; 604/284
[58] Field of Search ............................ 604/8, 175, 284

[56] References Cited

U.S. PATENT DOCUMENTS

| | | | |
|---|---|---|---|
| 2,624,341 | 1/1953 | Wallace | 604/284 |
| 3,663,965 | 5/1972 | Lee, Jr. et al. | 604/175 X |
| 3,765,032 | 10/1973 | Palma | 604/175 X |
| 4,015,601 | 4/1977 | Bobros et al. | 604/175 |
| 4,164,221 | 8/1979 | Bentley et al. | 604/175 X |
| 4,183,357 | 1/1980 | Bentley et al. | 604/175 |
| 4,217,664 | 8/1980 | Faso | 604/175 X |
| 4,350,157 | 9/1982 | Hoffa | 604/175 |
| 4,484,912 | 11/1984 | Raible | 604/175 |
| 4,512,761 | 4/1985 | Raible | 604/175 X |
| 4,534,760 | 8/1985 | Raible | 604/175 |
| 4,534,761 | 8/1985 | Raible | 604/175 |

Primary Examiner—George F. Lesmes
Assistant Examiner—Nancy A. B. Swisher

[57] ABSTRACT

An implant device having a passageway and an anchor means for establishing a biological anchor both formed from either pyrolitic carbon disposed or a graphite subtrate or virneous carbon. The passageway having an inlet inclined with respect to the passageway outlet from between 45 and 75 degrees.

1 Claim, 3 Drawing Figures

ANGULAR IMPLANT DEVICE

This is a division of application Ser. No. 624,801, filed June 26, 1984 now U.S. Pat. No. 4,534,760 which is a file wrapper continuation of Ser. No. 292,844 filed Aug. 14, 1981, now abandoned.

BACKGROUND OF THE INVENTION

The present invention relates to an implant device.

There are many situations in which it is necessary to perform an enterostomy on a patient. An enterostomy involves externalizing an internal vessel. Common vessels which commonly require externalizing are the ileum, colon, ureter, and bladder. Heretofore, enterostomies were accomplished by severing the vessel which was to be externalized and then suturing the wall of the vessel to an opening which has been formed on the surface of the body. The opening is normally formed on the abdomen. Generally, the wall of the vessel and the subdermal tissue and muscle surrounding the opening will grow together to permanently secure the vessel to the surface of the body. After the operation has healed, a container is attached to the surface of the skin. The container functions to receive the excrements which are discharged from the vessel.

DESCRIPTION OF THE DRAWINGS

Referring now to FIG. 1, an implant device, generally referred to as 1, includes a passageway, generally referred to as 3, and an anchor means for establishing a biological anchor. Anchor means 15 preferably includes a plurality of apertures 39 which promote fibro-vascular ingrowth 31. Passageway 3 includes an inlet section 5 initiated by an inlet 9 and terminated by an outlet 11. The axial centerline 35 passing through the center of the passageway inlet 9 is inclined with respect to the axial centerline 33 passing through the center of the passageway outlet 11 (indicated by the angle "x" in FIG. 1) from between about 45 and 75 degrees in order to connect implant device 1 to ureter 13 without occluding or kinking the ureter 13, thereby restricting or impeding flow therethrough.

In FIG. 1 the implant device 1 is illustrated as connected to a ureter 13 extending from kidney 21. The implant device is shown passing through skin 29, fat 27, fascia 25 and rectus 23 in attaching to ureter 13.

Figure 1:
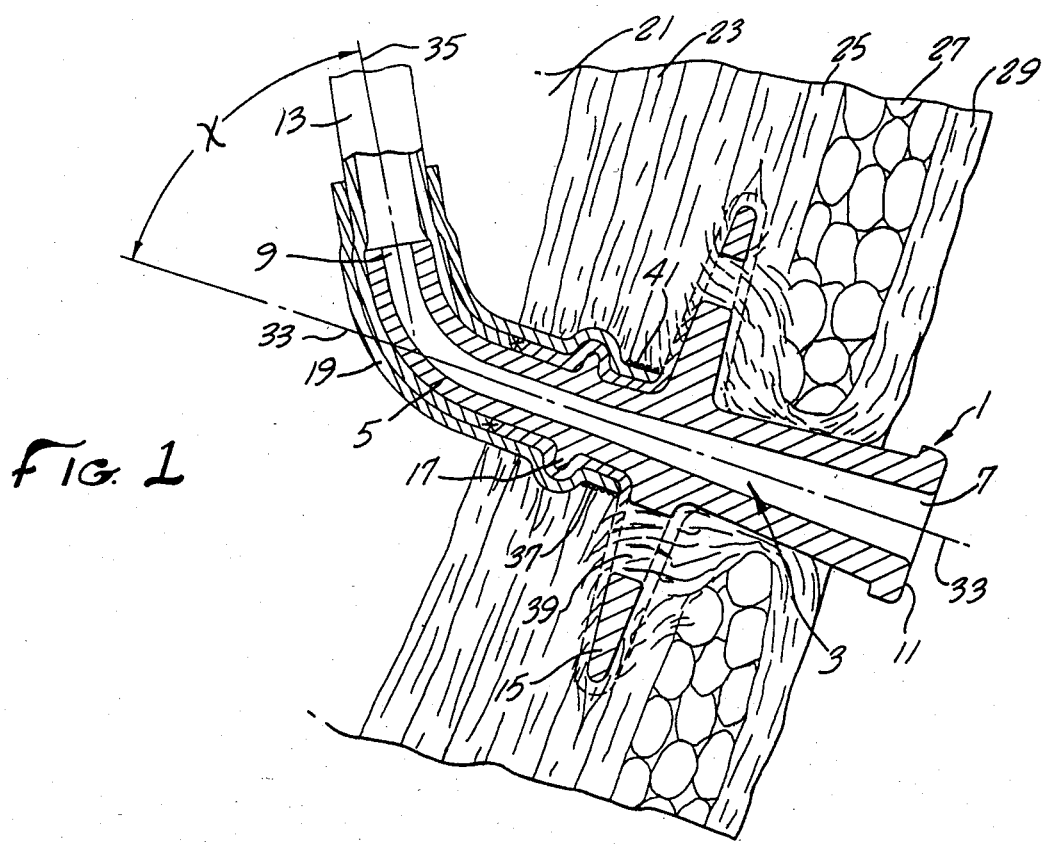
FIG. 1 is a cross-sectional view illustrating the implant device of this invention.

Implant device 1 also includes an annular rim 17 which forms an annular recess 37 between the annular rim 17 and the anchor means 15. This annular recess 37 allows for the securing of vascular grafting means 29 to implant device 1 as, for example, by means of suture 41.

The vascular grafting material means 19 is formed, for example, from Dacron, an E. I. du Pont de Nemours & Co. product of polyester' fiber. In a preferred embodiment at least a portion of the grafting material from which connector 1 is made is coated with collagen.

Figure 2:
FIG. 2 is a pictorial view illustrating an embodiment of the implant device of this invention.

Referring to FIG. 2, an embodiment is showing having two inlets sections 5a and 5b initiated with inlets 9a and 9b, respectively. The axial centerlines 35a and 35b passing through the centers of inlets 9a and 9b respectively, are each inclined (identified by angles "y" with respect to the axial centerline 33 passing through outlet 11 in FIG. 2) from between about 45 and about 75 degrees. This embodiment allows a single implant device 1 to be connected to two ureters 13.

Figure 3:
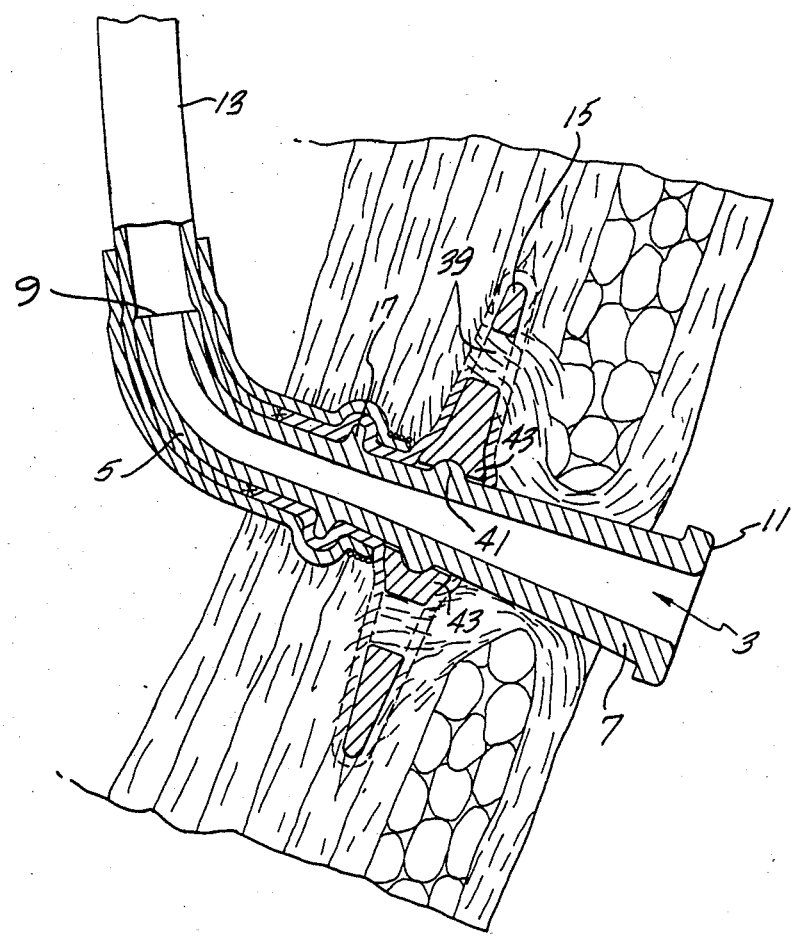
FIG. 3 is a partial cross-sectional view illustrating an embodiment of the implant device of this invention.

Referring now to FIG. 3, an embodiment of the implant device of this invention is shown wherein passageway 3 is rotatable with anchor means 15. Preferably anchor means 5 is secured about passageway 3 by means of the male 41 female 43 junction. The rotation of passageway 3 allows for connecting to ureter 13 without occluding or kinking the ureter and thereby restricting or impeding flow therethrough.

What is claimed is:

1. A urterostomy device comprising:

a passageway having an anchor means, both of which are formed from a material selected from the group consisting of (1) pyrolytic carbon disposed on a graphite substrate and (2) vitreous carbon, for attachment to an opened vessel;

said anchor means for establishing a biological anchor; and said passageway being further defined as having two substantially rigid inlet sections, each such inlet being initiated with a passageway outlet and having an outlet section terminated with a passageway outlet, said outlet section being in communication with said inlet section, wherein the axial centerline passing through the center of each passageway inlet is inclined with respect to the axial centerline passing through the center of said passageway outlet from between about 45 degrees and about 75 degrees.

* * * * *